(12) United States Patent
Rana et al.

(10) Patent No.: US 8,202,556 B2
(45) Date of Patent: Jun. 19, 2012

(54) TOPICAL COMPOSITION WITH SKIN LIGHTENING EFFECT

(75) Inventors: Jatinder Rana, Grand Rapids, MI (US); Ganesh Diwakar, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 12/977,708

(22) Filed: Dec. 23, 2010

(65) Prior Publication Data

US 2011/0123471 A1 May 26, 2011

Related U.S. Application Data

(62) Division of application No. 12/540,626, filed on Aug. 13, 2009, now Pat. No. 7,897,184.

(51) Int. Cl.
*A61K 36/00* (2006.01)
(52) U.S. Cl. .......................... 424/725; 424/769; 424/401
(58) Field of Classification Search .................... None
See application file for complete search history.

(56) References Cited

U.S. PATENT DOCUMENTS

| | | | |
|---|---|---|---|
| 5,478,579 A | 12/1995 | Sawruk | |
| 5,504,105 A | 4/1996 | Chiesi et al. | |
| 5,747,006 A | 5/1998 | Dornoff et al. | |
| 6,060,063 A | 5/2000 | Lansky | |
| 6,077,503 A | 6/2000 | Dronoff | |
| 6,103,240 A | 8/2000 | Zhou | |
| 6,291,533 B1 | 9/2001 | Fleischner | |
| 6,630,163 B1 | 10/2003 | Murad | |
| 6,733,797 B1 | 5/2004 | Summers | |
| 2002/0009506 A1 | 1/2002 | Tao | |
| 2003/0086986 A1 | 5/2003 | Bruijn et al. | |
| 2003/0091659 A1 | 5/2003 | Lu et al. | |
| 2003/0091665 A1 | 5/2003 | Lu et al. | |
| 2004/0059110 A1 | 3/2004 | Nakano et al. | |
| 2004/0151788 A1 | 8/2004 | Gluck et al. | |
| 2004/0162247 A1 | 8/2004 | Kim et al. | |
| 2005/0032882 A1 | 2/2005 | Chen | |
| 2005/0079232 A1 | 4/2005 | Offord-Cavin et al. | |
| 2005/0143366 A1 | 6/2005 | Pierce, Jr. et al. | |
| 2005/0176654 A1 | 8/2005 | Takagaki et al. | |
| 2005/0202103 A1 | 9/2005 | Rajendran et al. | |
| 2005/0227910 A1 | 10/2005 | Yang et al. | |
| 2005/0232901 A1 | 10/2005 | Zaghmout | |
| 2006/0051316 A1 | 3/2006 | Ohnogi et al. | |
| 2006/0211635 A1 | 9/2006 | Seeram et al. | |
| 2007/0116812 A1 | 5/2007 | Msika et al. | |
| 2008/0199545 A1 | 8/2008 | Krempin et al. | |
| 2008/0199546 A1 | 8/2008 | Krempin et al. | |
| 2009/0123578 A1 | 5/2009 | Crutchfield, III | |
| 2010/0028317 A1 | 2/2010 | Maes et al. | |

FOREIGN PATENT DOCUMENTS

| | | |
|---|---|---|
| CN | 1446549 | 10/2003 |
| CN | 2004/1026030 | 4/2004 |
| CN | 1490321 A | 4/2004 |
| CN | 1927364 A | 3/2007 |
| DE | 4330597 A | 9/1993 |
| EP | 1 441 686 B1 | 7/2008 |
| JP | 7196526 A | 8/1995 |
| JP | 1999/0049884 | 2/1999 |
| JP | 2000247896 | 9/2000 |
| JP | 2000256131 | 9/2000 |
| JP | 2001131053 A | 5/2001 |
| JP | 2002179585 A | 6/2002 |
| JP | 2006/117550 | 5/2006 |
| KR | 2003/0033393 | 5/2003 |
| KR | 2003/0057273 | 8/2003 |
| KR | 2003-0095669 | 12/2003 |
| KR | 2004-0038481 | 5/2004 |
| KR | 20040101694 | 12/2004 |
| KR | 10-0525994 B1 * | 11/2005 |
| KR | 10-710657 | 4/2007 |
| WO | WO 01/32191 A2 | 5/2001 |
| WO | WO 01/87315 A1 | 11/2001 |
| WO | WO 02/00236 A1 | 1/2002 |
| WO | WO 02/17909 A1 | 3/2002 |
| WO | WO 03/041636 A2 | 5/2003 |
| WO | WO 03/057141 A2 | 7/2003 |
| WO | WO 2004/091591 A2 | 10/2004 |
| WO | WO 2005/077396 A1 | 8/2005 |
| WO | WO 2006/079243 A1 | 8/2006 |

OTHER PUBLICATIONS

Chen et al., "Effects of *Celosia cristata* L. Flavonoid on Expression of Bone Morphogenetic Protein and Function of Tubular reabsorption of Rats with Diabetes Mellitus", Zhongguo Linchuang Kangfu (2005), 9(39), 188-190. (Abstract).

Chen, et al., "Green Tea Catechin Enhances Osteogenesis in a Bone Marrow Mesenchymal Stem Cell Line", Osteoporos Int. 16:2039-45 (2005).

(Continued)

*Primary Examiner* — Susan Hoffman
(74) *Attorney, Agent, or Firm* — Brinks Hofer Gilson & Lione; G. Peter Nichols

(57) ABSTRACT

A topical cosmetic composition for increasing skin whitening or lightening is described. The composition includes a pomegranate extract in an amount effective to reduce melanin composition. The pomegranate extract may be standardized to about 20% punicalagin. The composition may also include an extract from the genus *larix*, such as *Larix sibirica*. The *larix sibirica* may be standardized to 80% taxifolin. A method for using the compositions is described.

1 Claim, 3 Drawing Sheets

OTHER PUBLICATIONS

Gil, M. et al., "Antioxidant Activity of Pomegranate Juice and Its Relationship with Phenolic Composition and Processing", Journal of Agriculture and Food Chemistry, 48(10): 4581-4589 (2000). Printed from http://pubs.acs.org/doi/pdf/10.1021/jf000404a on Jul. 1, 2009. (Abstract).

Kropotov, A.V., et al., "Effects of Siberian Ginseng Extract and Ipriflavone of the Development of Glucocorticoid-Induced Osteoporosis", Bulletin of Experimental Biology and Medicine, vol. 133, No. 3, pp. 252-254 (Aug. 2002).

Makoto et al., "Grape Seed Pranthocyanidins Extract Promotes Bone Formation in Rat's Mandibular Condyle", European J. Oral Sci., (113): 47-52 (2005). (Abstract).

Ostrowska, et al., "Extra-Virgin and Refined Olive Oils Decrease Plasma Triglyceride, Moderately Affect Lipoprotein Oxidation Susceptibility and Increase Bone Density in Growing Pigs", J. Sci Food Agric. 86: 1955-63 (2006).

Patent Cooperation Treaty Search Report for PCT/US2007/022593, dated Jul. 23, 2008.

Patent Cooperation Treaty Search Report for PCT/US2007/022619, dated Aug. 21, 2008.

Puel, C, et al., "Olive Oil and its Main Phenolic Micronutrient (oleuropein) Prevent Inflammation-Induced Bone Loss in Ovariectomised Rat", Br. J. Nutrition, (94): 119-127 (2004).

Puel, et al., "Dose-Response Study of Effect of Oleuropein, an Olive Oil Polyphenol, in an Ovariectomy/Inflammation Experimental Model of Bone Loss in the Rat", Clinical Nutrition 25: 859-68 (2006).

Rana, J., et al., "Isolation and Analysis of Punicalaigns from Pomegranate fruit (*Punica granatum*): Punicalagins inhibit IL-1B stimulated RANKL gene expression in MG-63 cells (a human osteocarcoma cell line)". (Abstract) 2007.

Shimogaki et al., "In Vitro and In Vivo Evaluation of Ellagic Acid on Melangenesis Inhibition", International Journal of Cosmetic Science, 22(4): 291-303 (Dec. 2001). (Abstract) Printed from http://www3.intersciene.wiley.com/journal/120189503/abstract. on Jul. 1, 2009.

Tian et al., "Effect of Soybean Isoflavone on Expression of Bone BMP2 and TGF-.beta.1 in Ovariectomized Rats", Zhongguo Gonggong Weisheng Zazhishe (2004), 20(9), 1079-1080 (2005). Abstract.

Wang, Z.L. et al., Pharmacological Studies of the Large-Scaled Purified Genistein From Huaijiao (*Sophora Japonic-Leguminosae*) on Anti-Osteoporosis, Phytomedicine, 13 (9-10) pp. 718-723, (Nov. 2006).

Wattel et al., "Flavonoid Quercetin Decreases Osteoclastic Differentiation Induced by RANKL Via a Mechanism Involving NFkB and AP-1", J. Cell Biochem. 92: 285-95 (2004).

Yahara et al., "Mechanical Assessment of Effects of Grape Seed Proanthocyanidins Extract of Tibial Bone Diaphysis in Rats", J. Musculoskeletal Neuronal Interactions, (2): 162-169 (2005). (Abstract).

Yoshimura, M. et al., "Inhibitory Effect of an Ellagic Acid-Rich Pomegranate Extract on Tyrosinase Activity and Ultraviolet-Induced Pigmentation", Biosci. Biotechnol. Biochem. 69(12): 2368-2373 (2005).

Zhou et al., "Estrogens Activate Bone Morphogenetic Protein-2 Gene Transcription in Mouse Mesenchymal Stem Cells", Mol. Endocrinol., 17(1): 56-66 (Jan. 2003).

* cited by examiner

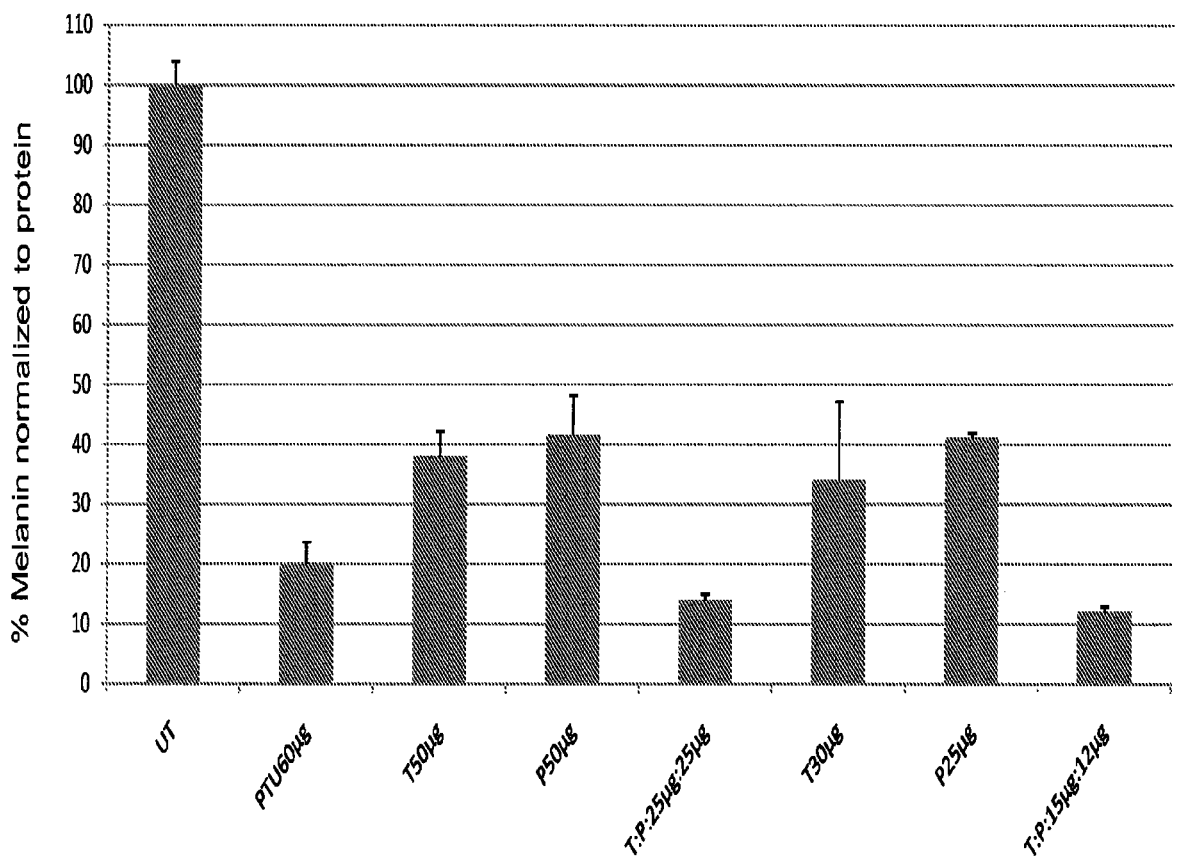

TOPICAL COMPOSITION WITH SKIN LIGHTENING EFFECT

This application is a divisional of U.S. patent application No. 12/540,626, filed Aug. 13, 2009, now U.S. Pat. No. 7,897,184.

BACKGROUND

The present invention relates to topical compositions to provide skin whitening or lightening effect.

Skin color is primarily determined by the amount of melanin in the skin. Melanin is a brown-black pigment present in the skin. Due to the dark color of the pigment, lower amounts of melanin result in lighter skin color while higher amounts result in darker skin color. Melanin is formed by the oxidation of the amino acid tyrosine to dihydroxyphenalanine in melanocytes. This reaction is catalyzed by the enzyme tyrosinase.

Excessive skin pigmentation may be caused by hormone abnormality in the human body, genetic diseases, etc., regardless of UV, or by excessive melanogenesis and melanin maldistribution due to excessive UV irradiation. A suitable amount of melanin in the skin has the positive effect of maintaining the skin healthy and absorbing UV, etc. However, excessive melanin results in negative effects, such as skin darkening and non-uniform skin color. Thus, many scientists have studied melanogenesis inhibition.

As a result of this pivotal role of tyrosinase in melanin formation, efforts to develop effective skin whitening compositions have focused on agents that inhibit the function and activity of tyrosinase. For example, compositions have been proposed that include a variety of known tyrosinase inhibitors, such as hydroquinone, vitamin C and its derivatives, kojic acid, arbutin, glutathione, cysteine, and mulberry extract, among others.

A problem with synthetic skin lighteners such as hydroquinone or kojic acid is that they may cause skin irritation or acute dermatitis. Thus, there is a continuing desire to incorporate natural sources into compositions in an attempt to address some of the undesirable aspects of synthetic products.

BRIEF SUMMARY

The present invention addresses some of the above issues. In one aspect of the invention, a topical composition is provided for reducing or inhibiting melanin production and it includes an effective amount of pomegranate extract. The composition can be used to whiten or lighten the skin. The pomegranate extract may be standardized to about 20% punicalagin.

Another aspect of the invention includes a topical composition that contains the combination of a pomegranate extract and an extract derived from the plant genus *Larix*, for example *larix sibirica* (Siberian larch) to reduce or inhibit melanin product resulting in skin whitening or lightening. In one aspect, the pomegranate extract is standardized to about 20% punicalagin and the *larix* extract is standardized to about 80% taxifolin. It has been found that surprisingly and unexpectedly the combination synergistically reduces or inhibits melanin production.

The present invention also relates to a method for whitening skin that includes applying to the skin compositions according to the present invention in an amount and for a period of time sufficient to whiten the skin.

It is to be understood that this invention is not limited to the particular compositions, methodology, or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

It is to be understood that, unless otherwise specifically noted, all percentages recited in this specification are by weight.

BRIEF DESCRIPTION OF THE DRAWINGS

FIG. 3 shows that the combination of a pomegranate extract and a Siberian larch extract synergistically reduces the melanin production.

DETAILED DESCRIPTION

Figure 2:
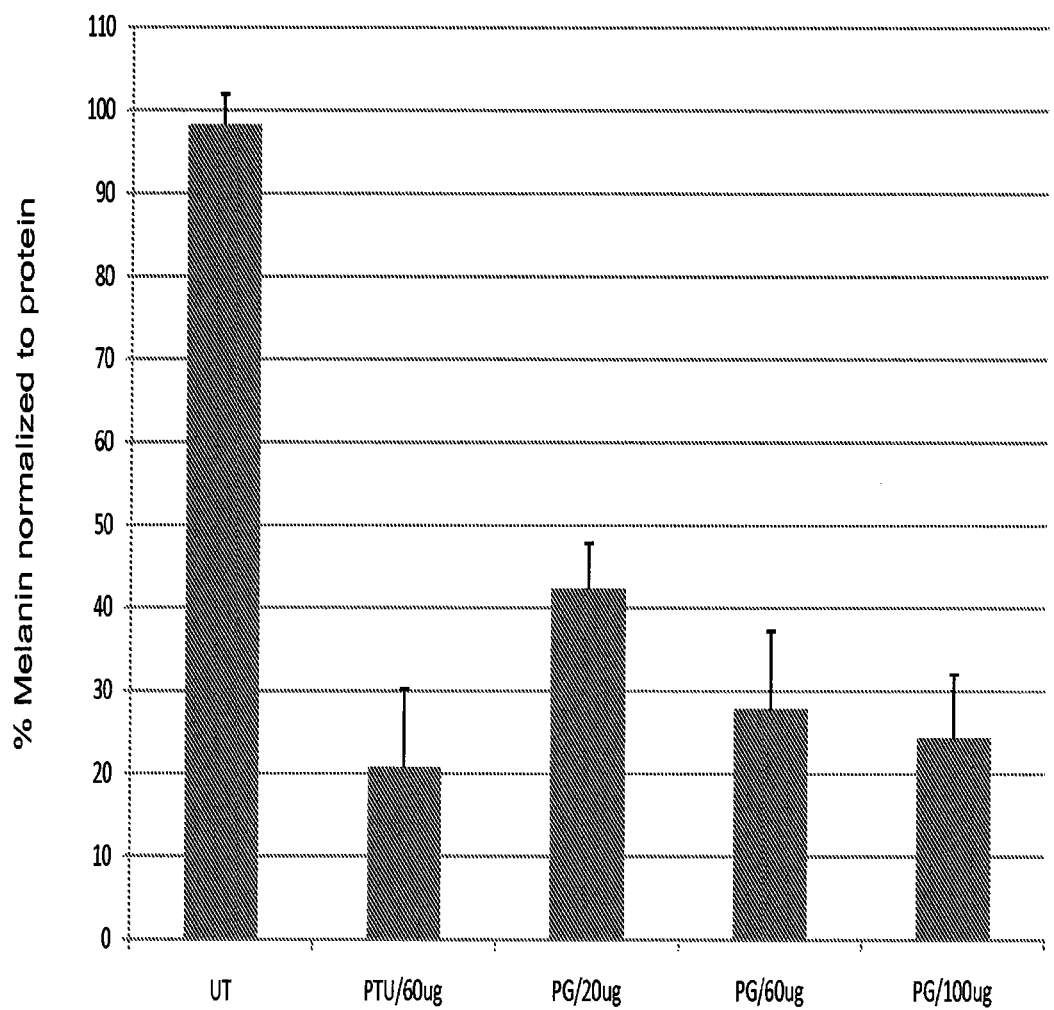
FIG. 2 shows the dose dependent reduction in melanin production with pomegranate extract standardized to 20% punicalagin.

The present invention is based on the surprising discovery that a pomegranate extract that is standardized to about 20% punicalagin provides a dose dependent effect on melanin production. As shown in FIG. 2, melanin production is increasingly reduced or inhibited with an increase in the dose of pomegranate extract.

Accordingly, one aspect of the present invention provides a topical composition that includes a pomegranate extract in sufficient amounts to achieve a reduction in melanin production.

Pomegranate Extract

Pomegranates can be extracted to yield an extract of pomegranate (pomegranate extract) that is useful in unique compositions of the present invention. When extracted, pomegranate, known as *Punica granatum*, is standardized to punicalagin content. For example, the pomegranate extract is standardized to about 20% punicalagin content. Punicalagins exist as isomers of 2,3,hexahydroxydiphenoyl-gallagyl-D-glucose. An exemplary structure is shown below:

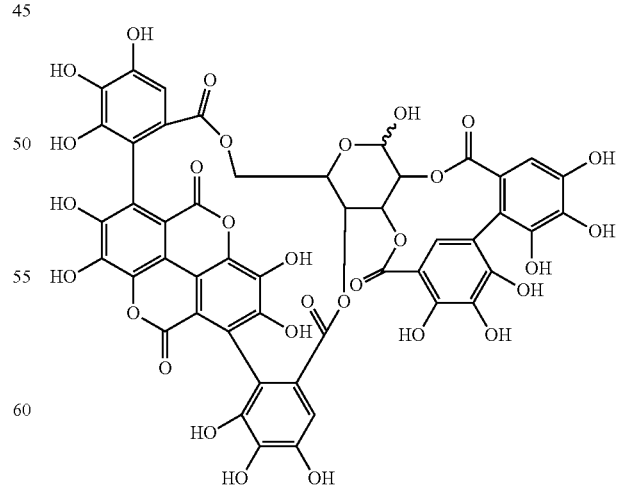

While it is known that in an acidic environment punicalagin may hydrolyze to ellagic acid, the compositions in which the pomegranate extract is used have a generally neutral pH.

Thus, the pomegranate extract in the compositions of the present invention are not hydrolyzed to ellagic acid. Nevertheless, it has been found that the pomegranate extract that has been standardized to about 20% punicalagin provides a dose dependent reduction in melanin production.

Pomegranate extracts may be commercially obtained from various sources including Nature's Way (Springville, Utah), Nature's Herbs (American Fork, Utah), Swansen's Health Products (Fargo, N. Dak.) and Doctor's Trust Vitamins (Orlando, Fla.). In addition, a suitable pomegranate extract may be obtained using any of the extraction techniques discussed more fully below or known in the art.

The pomegranate extract useful in the composition of the present invention is standardized to about 20% punicalagin. One of skill in the art will appreciate that the extract may be standardized to other levels of punicalagin. For example, the pomegranate extract could be standardized to about 25%, 30%, 35%, 40%, 45%, 50%, 55%, 60%, 65%, 70%, 75%, 80%, 85%, 90%, or 95% punicalagin content.

The pomegranate extract may be incorporated into the compositions of the present invention in an amount from about 0.001% to about 10%, or in an amount from about 0.01% to about 5% when standardized to about 20% punicalagin. Of course, one of skill in the art will appreciate that the amount of the extract incorporated into the composition may depend on the standardized content of punicalagin. Thus, if the pomegranate extract is standardized to about 40% punicalagin, the above described amounts of the pomegranate extract will be reduced by one-half, e.g., in an amount from about 0.0005% to about 5%.

Another aspect of the present invention includes combining the pomegranate extract described above with a *larix* extract (e.g., *Larix sibirica*, Siberian larch). Surprisingly and unexpectedly it was found that the combination provided greater than expected melanin inhibition and thus an increase in skin whitening or lightening.

*Larix* Extract

The plant genus *Larix* refers generally to any of the numerous conifers that have deciduous needlelike leaves. The *Larix* genus may include at least the following species: *Larix amabilis, Larix americana, Larix amurensis, Larix cajanderi, Larix czekanowskii, Larix dahurica, Larix decidua, Larix eurolepis, Larix europaea, Larix gmelinii, Larix griffithiana, Larix griffithii, Larix himalaica, Larix japonica, Larix kaempferi, Larix kamtschatica, Larix kongboensis, Larix koreana, Larix kurilensis, Larix laricina, Larix leptolepis, Larix lyaffii, Larix mastersiana, Larix occidentalis, Larix olgensis, Larix potaninii, Larix principis-rupprechtii, Larix russica, Larix sibirica, Larix speciosa, Larix sukaczewii.*

A desirable extract obtained from *Larix* and, in particular from *Larix sibirica* (Siberian larch) includes taxifolin. When extracted the *Larix* extract is standardized to about 80% taxifolin content. Taxifolin (also referred to as dihydroquercetin) has the following structure:

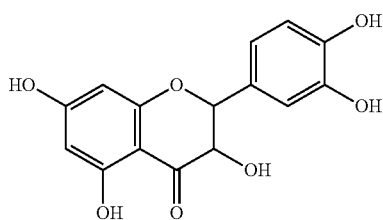

*Larix* extracts, particularly Siberian larch extracts may be commercially obtained from various sources including Lalilab Inc., 1415 Hamin Rd, Durham, N.C. 27704, USA. In addition, a suitable *Larix* extract may be obtained using any of the extraction techniques discussed more fully below or known in the art.

As noted above, the *Larix* extract is standardized to about 80% taxifolin. One of skill in the art will appreciate that the extract may be standardized to other levels of taxifolin. For example, the *Larix* extract could be standardized to about 25%, 30%, 35%, 40%, 45%, 50%, 55%, 60%, 65%, 70%, 75%, 80%, 85%, 90%, or 95% taxifolin content.

The *Larix* extract may be incorporated into the composition of the present invention in an amount from about 0.001% to about 10%, or in an amount from about 0.01% to about 5%. Of course, one of skill in the art will appreciate that the amount of the extract incorporated into the composition may depend on the standardized content of taxifolin. Thus, if the *Larix* extract is standardized to about 40% taxifolin, the above described amounts of the *Larix* extract will be reduced by one-half, e.g., in an amount from about 0.0005% to about 5%.

Exemplary Extraction Processes

In one example, an extract useful in the unique compositions of the present invention might be obtained using an organic solvent extraction technique. In another example, solvent sequential fractionation may be used to obtain an extract useful in the unique compositions of the present invention. Total hydro-ethanolic extraction techniques might also be used to obtain an extract useful in the unique compositions of the present invention. Generally, this is referred to as a lump-sum extraction. The extract generated in this process will contain a broad variety of phytochemicals present in the extracted material including fat and water solubles. Following collection of the extract solution, the solvent will be evaporated, resulting in the extract.

Total ethanol extraction may also be used in the present invention. This technique uses ethanol, rather than hydro-ethanol, as the solvent. This extraction technique generates an extract that may include fat soluble and/or lipophilic compounds in addition to water soluble compounds.

Another example of an extraction technique that might be used to obtain an extract useful in the present invention is supercritical fluid carbon dioxide extraction (SFE). In this extraction procedure the material to be extracted is not exposed to any organic solvents. Rather, the extraction solvent is carbon dioxide, with or without a modifier, in supercritical conditions (>31.3° C. and >73.8 bar). Those of skill in the art will appreciate that temperature and pressure conditions can be varied to obtain the best yield of extract. This technique generates an extract of fat soluble and/or lipophilic compounds, similar to the total hexane and ethyl acetate extraction technique described above.

Those of skill in the art will appreciate that there are many other extraction processes, both known in the art and described in various patents and publications that can be used to obtain the extracts to be used in practicing the present invention. For example, the extraction procedures described in the following references, which are incorporated herein by reference, could be used in practicing the present invention: Murga et al., "Extraction of natural complex phenols and tannins from grape seeds by using supercritical mixtures of carbon dioxide and alcohol." *J. Agric Food Chem.* 2000 August:48(8):3408-12; Hong et al., "Microwave-assisted extraction of phenolic compounds from grape seed." *Nat Prod Lett.* 2001; 15(3):197-204; Ashraf-Khorassani et al., "Sequential fractionation of grape seeds into oils, polyphenols, and procyanidins via a single system employing $CO_2$-based fluids." *J. Agric Food Chem.*, 2004 May 5; 52(9):2440-4.

Figure 1:
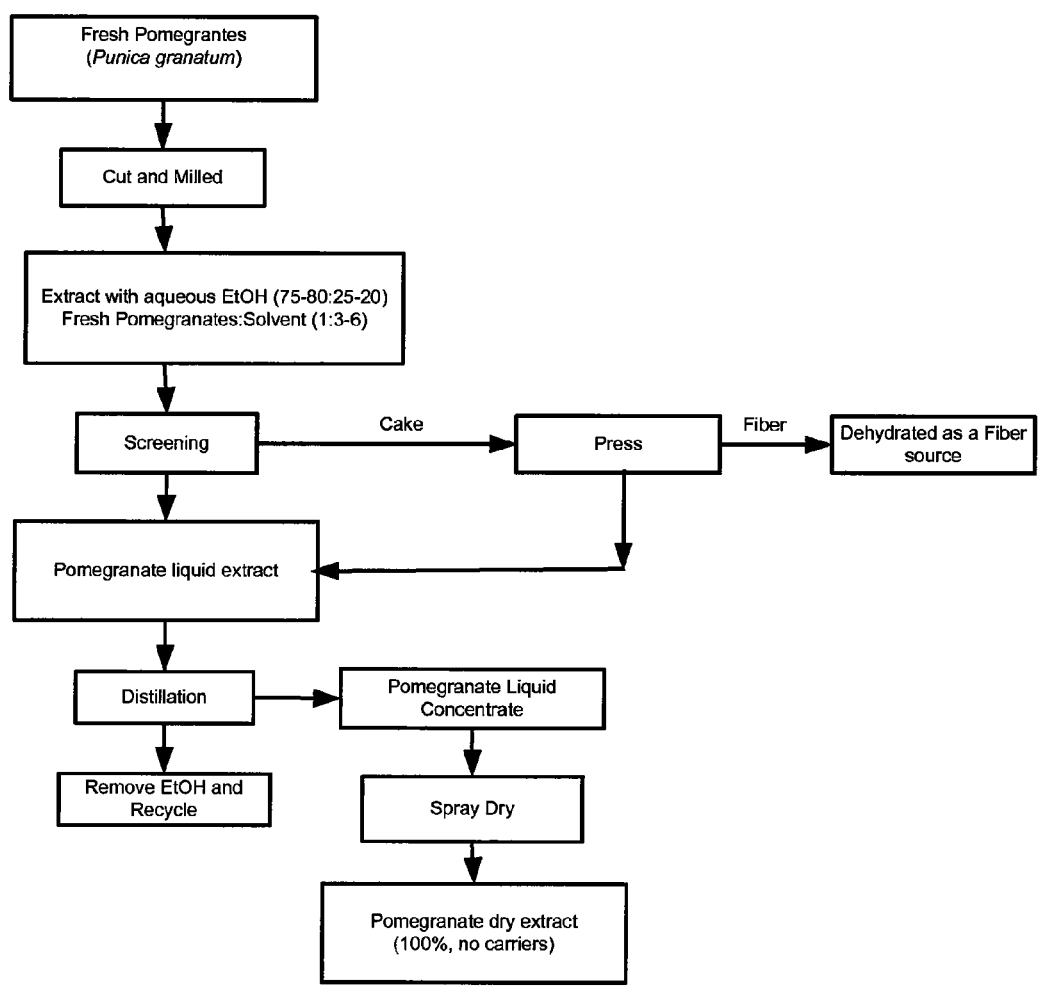
FIG. 1 shows an exemplary process for producing a pomegranate extract useful in the present invention.

According to one example of the present invention, the pomegranate extract is obtained according to the process shown in FIG. 1. In this process, fresh pomegranates are harvested, cut, and milled. Thereafter, the milled pomegranates are extracted with an aqueous ethanol extractant containing from about 75 to 80% water and from about 25 to 20% ethanol, with the ratio of the milled pomegranate to extractant in the range from about 1:3 to about 1:6.

The product is screened or filtered to create a supernatant and a cake. The cake can be pressed to remove a substantial portion of the liquid, which can be added to the supernatant. The cake can then be dehydrated and used as fiber source. The supernatant may then be distilled to remove the ethanol, which can be recycled as part of the extractant and to form a pomegranate liquid concentrate. The concentrate is dried such as by spray drying to provide a dried pomegranate extract that can be assayed and standardized to about 20% punicalagin.

Compositions of the Invention

Compositions of the present invention may be formulated in an acceptable carrier and may be prepared, packaged, and labeled for increasing skin whitening or lightening, inhibiting or decreasing, or reducing melanogenisis, melanin, or pigmentation.

In one example, the invention is a composition for increasing skin whitening or lightening comprising an effective amount of a pomegranate extract to reduce melanin production. The pomegranate extract may be standardized to about 20% punicalagin. The composition may include a cosmetically acceptable vehicle. The composition may have a pH between about 6.0 to about 8.0, or alternatively the composition may have a pH that is substantially neutral.

In another example the invention is a composition for increasing skin whitening or lightening comprising a combination of an effective amount of a pomegranate extract and an effective amount of a Siberian larch extract, wherein the combination reduces or inhibits melanin production. The pomegranate extract may be standardized to about 20% punicalagin. The Siberian larch may be standardized to about 80% taxifolin. The composition may include a cosmetically acceptable vehicle. The composition may have a pH between about 6.0 to about 8.0, or alternatively the composition may have a pH that is substantially neutral. It is to be understood that the composition may include each above alternatives individually, or in one or more combinations.

In another example, the invention is a composition for increasing skin whitening or lightening comprising a combination of a pomegranate extract and a Siberian larch extract, wherein the combination increases the whiteness or lightness of skin and such that the pomegranate extract is standardized to about 20% punicalagin and the Siberian larch is standardized to about 80% taxifolin.

In another example, the invention is a composition for increasing skin whitening or lightening comprising a combination of a pomegranate extract and a Siberian larch extract, wherein the combination increases the whiteness or lightness of skin and such that the pomegranate extract is present in an amount from about 0.001% to about 10% and the Siberian larch is present in amount from about 0.001% to about 10%.

In one example, the invention includes a composition containing a combination of a pomegranate extract and a Siberian larch extract where each extract is present in a ratio from about 1:2 to about 2:1 and in one example each is present in a ratio of about 1:1.

In a further example, the invention is a method of increasing or skin whitening or lightening that comprises administering to the subject a composition that includes a combination of a pomegranate extract and a Siberian larch extract, wherein the combination reduces or decreases melanogenisis, pigmentation, or both.

The compositions of the invention may be administered topically. In general, the combinations of the invention are included in a cosmetically acceptable vehicle. Examples of cosmetically acceptable vehicles suitable for all embodiments of the present invention include, but are not limited to, water, glycerin, various alcohols such as ethanol, propyl alcohol, vegetable oil, mineral oil, silicone oils, fatty ethers, fatty esters, fatty alcohols, glycols, polyglycols or any combinations thereof. Methods of formulation are well known in the art and are disclosed, for example, in Remington's Pharmaceutical Sciences, Gennaro, Mack Publishing Co., Easton Pa., 1990, which is incorporated herein by reference.

The compositions of the present invention may be formulated in any convenient form suitable for topical application to the skin. Such forms include aerosol spray, gel, cream, dispersion, emulsion, foam, liquid, lotion, mousse, patch, pomade, powder, pump spray, solid, solution, stick or towelette. Suitable emulsions include oil-in-water, water-in-oil, and water-in-silicone emulsions.

The compositions may be administered as needed, daily, several times per day or in any suitable regimen such that the desired outcome is achieved. In the method, the frequency of topical applications will depend on several factors, including the desired level of suppression of melanogenesis. A suitable regimen includes application to the skin twice daily, with one application in the morning and one in the evening. The amount of the composition used in each application will also depend on several factors, including the desired level of suppression of melanogenesis and the content of the extract in the composition.

EXAMPLES

Example 1

Pomegranate Extract Standardized to 20% Punicalagin Demonstrated Dose Dependent Reduction of Melanin Production To determine if the punicalagin present in pomegranate affected melanin production, the following assay was performed. Standardized pomegranate extract containing 20% punicalagin was tested. The pomegranate extract in an amount of 20 µg, 60 µg, and 100 µg was solubilized in DMSO and added to Melan-a cells that were freshly seeded at a density of $5 \times 10^4$ cells on a 24 well plate. The cytosolic pH of the Melan-a melanocytes in this assay is about 6.8 and thus, it is believed that the punicalagin present in the tested pomegranate extract does not hydrolyze to ellagic acid. Each dose of the pomegranate extract was added to the cells in triplicate. The final concentration of DMSO in the culture medium was maintained at 0.25%. Forty eight hours following the first set of treatment, the cells were again treated with the pomegranate extract and supplemented with fresh medium. Two days later, melanin was extracted and quantified by normalizing with protein content, following the method described by Komatsu et al. (Pigment Cell Res. 2005, 18:447).

Inhibitory activity of samples was reported as % reduction in melanin production compared to 100% untreated control (UT). Phenylthiourea (PTU) a well known tyrosinase inhibitor was used as positive inhibitor control in the assay. FIG. 2 plots the results. It can be seen that the use of a pomegranate extract standardized to 20% punicalagin provided a dose dependent reduction in melanin production.

Example 2

Pomegranate Extract and Siberian Larch Synergistically Reduce Melanin Production To determine the effect of the combination of a pomegranate extract and Siberian larch on melanin production the following assay was conducted. The test compositions listed in Table 1 were solubilized in DMSO and added to Melan-a cells that were freshly seeded at a density of $5 \times 10^4$ cells on a 24 well plate. The cytosolic pH of the Melan-a melanocytes in this assay is about 6.8 and thus, it is believed that the punicalagin present in the tested pomegranate extract does not hydrolyze to ellagic acid. Each dose of the test composition was added to the cells in triplicate. The final concentration of DMSO in the culture medium was maintained at 0.25%. Forty eight hours following the first set of treatment, the cells were again treated with the test composition and supplemented with fresh medium. Two days later, melanin was extracted and quantified by normalizing with protein content, following the method described by Komatsu et al. (Pigment Cell Res. 2005, 18:447).

TABLE 1

| Test Composition | Amount (µg) |
| --- | --- |
| Phenylthiourea (PTU) | 60 |
| Siberian Larch extract (standardized to 80% Taxifolin) | 50 |
| Siberian Larch extract (standardized to 80% Taxifolin) | 30 |
| Pomegranate extract (standardized to 20% punicalagin) | 50 |
| Pomegranate extract (standardized to 20% punicalagin) | 25 |
| Combination of Siberian Larch extract (standardized to 80% Taxifolin) and Pomegranate extract (standardized to 20% punicalagin) | 25 of Siberian Larch extract and 25 of Pomegranate extract |
| Combination of Siberian Larch extract (standardized to 80% Taxifolin) and Pomegranate extract (standardized to 20% punicalagin) | 15 of Siberian Larch extract and 12 of Pomegranate extract |

Inhibitory activity of samples was reported as % reduction in melanin production compared to 100% untreated control (UT). Phenylthiourea (PTU) a well known tyrosinase inhibitor was used as positive inhibitor control in the assay. FIG. 3 plots the results. It can be seen that when compared to Siberian Larch extract standardized to 80% taxifolin and tested at 50 µg/ml and 30 µg/ml alone and to Pomegranate extract standardized to 20% punicalagin and tested at 50 µg/ml and 25 µg/ml, the combination of Pomegranate extract and Siberian Larch extract in a substantially 1:1 ratio to provide a total of 50 µg/ml and 27 µg/ml of tested composition provided a greater than two fold reduction in melanin production.

It is intended that the foregoing detailed description be regarded as illustrative rather than limiting, and that it be understood that it is the following claims, including all equivalents, that are intended to define the spirit and scope of this invention.

The invention claimed is:

1. A method of whitening skin comprising topically applying to the skin a composition comprising a pomegranate extract standardized to 20% punicalagin in an amount from about 0.001% to about 10% and a Siberian larch extract standardized to 80% taxifolin and present in an amount from about 0.001% to about 10%, wherein the pomegranate extract and the Siberian larch extract are included in a ratio of about 1:1 that is effective to reduce melanin synthesis, wherein the composition has a pH between about 6.0 and 8.0, and wherein the composition is applied in an amount and for a period of time sufficient to visibly whiten the skin.

* * * * *